United States Patent [19]
Holm-Kennedy et al.

[11] Patent Number: 4,885,623
[45] Date of Patent: Dec. 5, 1989

[54] DISTRIBUTED CHANNEL-BIPOLAR DEVICE

[76] Inventors: James W. Holm-Kennedy, 3215 Pacific Hts. Rd., Honolulu, Hi. 96813; David N. Okada, 1717 S. Dorsey Ln., #2110, Tempe, Ariz. 85281

[21] Appl. No.: 114,608

[22] Filed: Oct. 30, 1987

[51] Int. Cl.[4] .................. H01L 29/72; H01L 27/02; H01L 29/66; H01L 27/14
[52] U.S. Cl. ........................... 357/34; 357/43; 357/25; 357/30; 357/23.1
[58] Field of Search ............... 357/43, 23.4, 16, 25, 357/30 I, 34

[56] References Cited

U.S. PATENT DOCUMENTS

| | | | |
|---|---|---|---|
| 4,630,084 | 12/1986 | Tihanyi | 357/23.4 |
| 4,748,484 | 5/1988 | Takakuwa et al. | 357/16 |

OTHER PUBLICATIONS

Reddi, "Influence of Surface Conditions on Silicon Planar Transistor Current Gain", SOLID-STATE ELECTRONICS, Pergamon Press, 1967, vol. 10, pp. 305-334.

Chih-Tang Sah, "Effect of Surface Recombination and Channel on P-N Junction and Transistor Characteristics", IRE TRANSACTIONS ON ELECTRON DEVICES, January 1962, pp. 94-108.

Primary Examiner—Rolf Hille
Assistant Examiner—Robert P. Limanek
Attorney, Agent, or Firm—James Creighton Wray

[57] ABSTRACT

A merged channel and bipolar device which exploits the distributed character of the device generates useful electronic characteristics by controlling the current and voltage inputs to the four or more terminals attached to the device, said electronic characteristics being useful for affecting the ac and dc current gain of the device, its transconductance, non-linearities, the electronic output characteristics as a function of input signals, electronic switching, gain control, output limiting, heterodyning, harmonic generation and voltage references.

Other applications which employ non-linear behavior include distributed amplification of traveling waves, multiple methods for chemical sensing and other sensor applications. The device behavior can be strongly affected by the device's distributed nature with bipolar behavior and FET behavior substantially different in different regions of the device, and the onset and distribution of this heterogenious behavior being affected directly by the input electrical voltages and currents. Channel geometry and conductivity and gate shape (where a gate is employed) can be used to affect the desired electrical performance. Sensing applications can be affected by intentional modification of surface parameters such as surface recombination, velocity, and by choice of gate materials and gate shape where a gate is used.

Applications of the device encompass electrical parameter generation useful for circuit applications. An example is the generation of an accurate reference voltage $V_{thg}$ and constant current values, and transducing and sensing applications for sensing chemicals, magnetic fields, forces, pressure, and other tranducing stimuli.

42 Claims, 13 Drawing Sheets

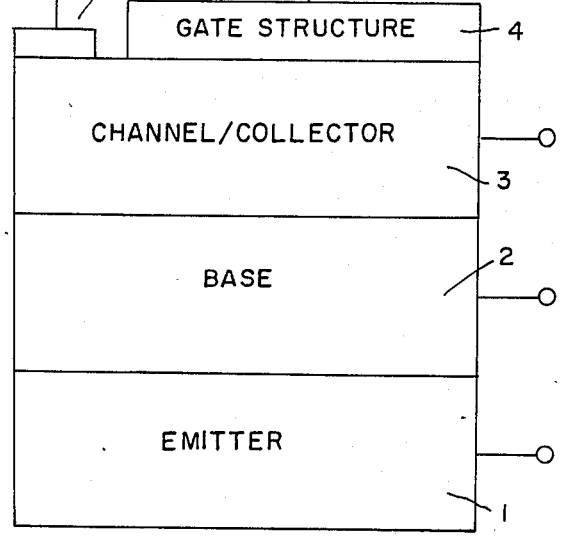
FIG. 1a
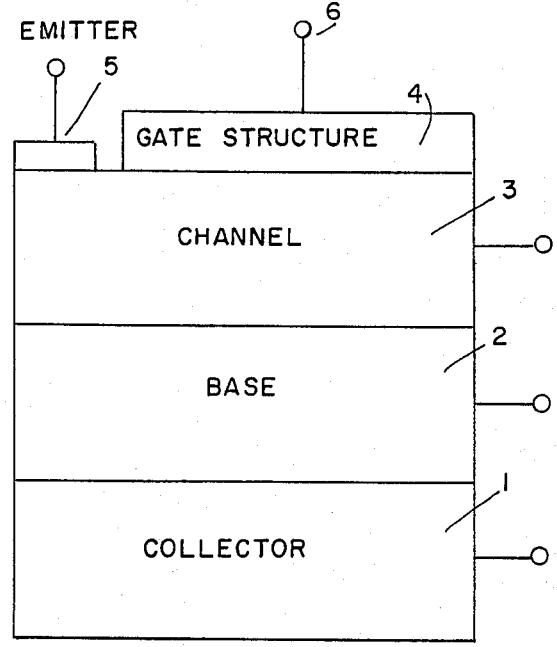
FIG. 1b
FIG. 2

DISTRIBUTED CHANNEL-BIPOLAR DEVICE

Background of the Invention

At the present time, electronic devices for the most part consist of lumped devices represented by lumped circuit parameters. Examples of such discrete devices of this nature and which have profound and diverse application in electronics are the MOSFET, the BJT (bipolar junction transistor), the MESFET (metal semiconductor FET) and JFET (junction field effect transistor). These and other discrete devices are connected in various ways (circuits) to generate particular electronic functions such as amplification, harmonic generation, optical and chemical sensing, switching, logic functions, etc. Each such device and its interconnects, when placed in an integrated circuit (IC), use up valuable area on the semiconductor wafer surface. And, usually, the more devices used to achieve a particular electronic behavior, the higher the noise level, power dissipation and the more the parasitic degradation of various useful parameters, such as speed. The acquisition of useful, sometimes complex, electrical characteristics in a single device or a few devices rather than in a large and complex circuit made up of many devices thus can improve performance, reduce size and cost, and in some cases generate electrical characteristics which may not be achievable with discrete devices, or may provide improvements over discrete performance.

Electrical parameters which act as reference values are useful. Among such useful parameters are reference voltages and constant current values. The present device can be operated so as to provide both of these parameters.

Summary of the Invention

The present invention is an electronic device of a merged and distributed character. Its purpose is to provide particular electronic functions which are useful for chemical and other sensing, such as pressure sensing and force sensing, optical sensing, magnetic sensing and other types of sensing; and to provide a method of amplification of current, voltage and optical or other waves, and to provide a method to produce and control non-linearities and other electronic functions. To achieve this purpose, a conducting channel (which may or may not be controlled by a gate) and an underlying pn or np structure are used. The channel acts as either a distributed collector or distributed emitter of a BJT and can be operated with appropriate biases, such that the operation of the device causes distributed and inhomogeneous behavior with the inhomogeneous behavior providing useful electronic function. The inhomogeneous behavior may consist of regions of operation in the same total structure where there simultaneously exists BJT saturation behavior in one region, simultaneous forward active BJT behavior in another region, and a transitional behavior in a third region. It is intended that the partitioning of these regions can be meaningfully affected by various bias parameters including gate voltage and base current $I_B$.

It is also intended that the gate or channel geometry can be chosen to select or enhance the desirable electronic behavior.

One object of the invention is to provide a method of chemical sensing where a gate or surface is prepared in a manner to be chemically sensitive and to affect the device's electronic behavior.

Another object of the invention is to be able to chemically sense by inspecting the transconductance threshold voltage $V_{THG}$ which is related to the MOS threshold ($V_{TH}$), but which can be determined to a much greater precision than $V_{TH}$ and determined via a null measurement with great sensitivity.

Another objective of the invention is to be able to measure the transconductance $g_m$ vs. a gate voltage Vg, or at a particular Vg, such that the effect of a chemical species on the gate can be measured with great sensitivity.

A further objective of the device is to use it in such a manner that it can be interrogated using the base current in order to determine the influence of an absorbed chemical species on the gate or on the channel surface.

Another objective of the device is to use the dependence of the ac current gain $\beta ac$ on $I_B$ or on Vg or on other parameters to sense and quantify the influence of an absorbed chemical on the surface.

A further objective of the device is to provide a means to sense one or more chemicals absorbed onto a gate or channel surface and to identify the species by the photon energy (wavelength) necessary to dissociate the chemical species from the gate or channel surface, and to qualitatively and quantitatively detect the dissociation of the species. And, by varying the photon energy of the device, to qualitatively and quantitatively detect the dissociation of one or more chemical species from the gate or channel surface of the device. Thus, the device can be reset using light and the chemical species identified using light. To accomplish this, specific chemical binding to surface defects or to a material on the gate can be employed, where different chemicals have with different energies.

A further objective of the device is to qualitatively and quantitatively detect chemical species by inspection of the change in the non-linear behavior of the device, such as the height, width, and location of a harmonic of a small or large input AC signal which has been applied to one of the device terminals, or by measuring the non-linear parameters such as heterodyne gain, or by other non-linear means. Included in the various methods designed to achieve the above are sweeping the base current or gate voltage, applying dc and ac voltages and/or currents to one or more of the four device terminals and inspecting the resulting electronic characteristics and their alteration with absorbed chemical species, light etc.

Another objective of the device is to sense other quantities such as light, temperature, pressures or other force by interrogating the device in methods identical or similar to those referred to for chemical sensing.

Still another objective of the device is to use a chemically active material such as polymide on the gate to detect water vapor or other chemicals.

A further objective of the device is to use the effect of chemicals (including water vapor) or light or heat to affect the surface (or interface) surface recombination velocities of the channel surface, thereby altering the device characteristics and thereby sensing the absorbed chemical or absorbed light, or other tranduction stimulus.

Another objective of the device is to use the spatial geometry and the distributed effects to measure photoabsorption of light of different wavelengths where the light is spatially distributed along the surface region from the drain/collector contact out along the channel. For example, incident light can be spatially distributed by wavelength using diffraction or a prism or other means, such that, e.g., green light falls near the drain/collector contact, red light falls on the absorbing surface farthest from said contact, and yellow light falls in between. The device may have no gate metal, only a transparent oxide and a doped channel, or the gate may be of a transparent material such as InSnO (ITO).

A further objective of the device is to provide a spatial detector of a light beam which has been split according to wave lengths and which allows for the accurate discrimination of any wavelength components of the original beam, thus creating an optical multichannel analyzer effect, or a spectrometer on a single chip in a single device.

Another objective of the device is to use a gate geometry on a MOS gate structure (or JFET or MESFET gate structure) to affect the device's electrical behavior in such a way as to provide an ac gain $b_{ac}$, ($I_{Bo}$) dependence on dc base current $I_{Bo}$, such that a continuous range of $b_{AC}$ is addressable, or such that a number of discrete values of $b_{AC}$ can be addressed by selection of $I_{Bo}$ or $V_{gO}$.

A further objective of the device is to provide a means to generate the desired power dependence of $I_C$ on $I_B$ or $I_C$ on $V_g$ or other (first) parameter dependence on a second parameter with a functional dependence (such as square law, exponential, etc.) that makes the device especially useful for logic circuits and analog circuits.

A further objective of the device is to use the spatial distribution of the amplifying state (such as the forward active region) to amplify a wave traveling along the gate or channel away from or towards the drain, and to control the amount of gain or attenuation by controlling the ac gain via the active amplifying area fraction. The objective of use for amplifying optical and microwaves, and acoustic waves is also intended. For example, a corrugated (slow wave structure) gate with a field component arising from a traveling electromagnetic wave can be amplified over the forward active region of the distributed device.

Another objective of the device is to use a homojunction or heterojunction structure to inject minority carriers into the base channel and to amplify an optical wave travelling through the inverted population region. Here, the saturation region will provide the largest amplification if population inversion is present. By affecting the distribution of the forward active and saturation regions, the gain can be controlled.

Another objective of the device is to provide a controlled attenuation of a wave where the forward active and saturation regions provide different amounts of attenuations.

Another objective of the device is to use the non-linear effects related to traveling waves to mix two different waves, generate harmonics and to provide other useful non-linear functions.

A further objective of the device is to use the channel as an emitter and affect the emitter (channel) base bias by controlling the channel voltage drop via externally applied input, such as the base current or gate voltage. A variety of applications similar to those already stated above are also part of the objectives of the device when biased into this mode (channel as emitter), using the distributed effects of the device.

A further objective of the device is to place a variety of different materials contiguously along the gate with different materials having different chemical sensitivities and specificities, and to use the control of the distributed behavior of the device to identify type and concentration of the absorbed chemical species in a single distributed device.

Another objective of the device is to use it in both a discrete manner and a distributed manner to provide a precise transconductance threshold voltage ($V_{THG2}$) $V_{THG}$. In using the channel as an emitter or channel as a collector, $V_{thg}$ or $V_{thg2}$ can provide a reference voltage, an accurate and precise chemically sensitive threshold voltage, an accurate temperature sensitive threshold voltage, for an accurate sensitive threshold voltage, and for other transduction applications where the device has been fabricated to have the threshold voltage $V_{THG}$ be sensitive to the parameter of interest, e.g., to a chemical species, pressure, temperature, etc.

BRIEF DESCRIPTION OF THE DRAWINGS

FIG. 1 is a schematic representation of the merged and distributed channel/BJT device. FIG. 1A shows the configuration with the channel functioning as a distributed collector. FIG. 1B shows the device configuration with the channel as a distributed emitter.

FIG. 2 is a cross-section of the MOSBJT.

DETAILED DESCRIPTION OF THE DRAWINGS

Figure 3:
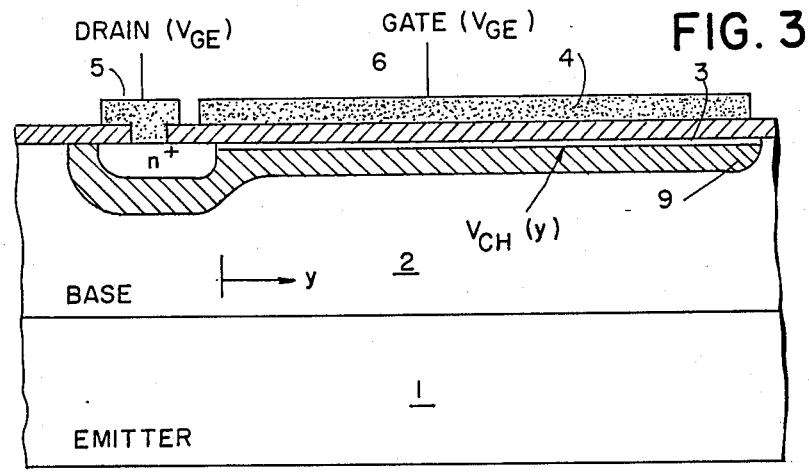
FIG. 3 is a cross-sectional diagram of the forward active biased MOSBJT with the invention layer present under various conditions of drain bias.
Figure 4:
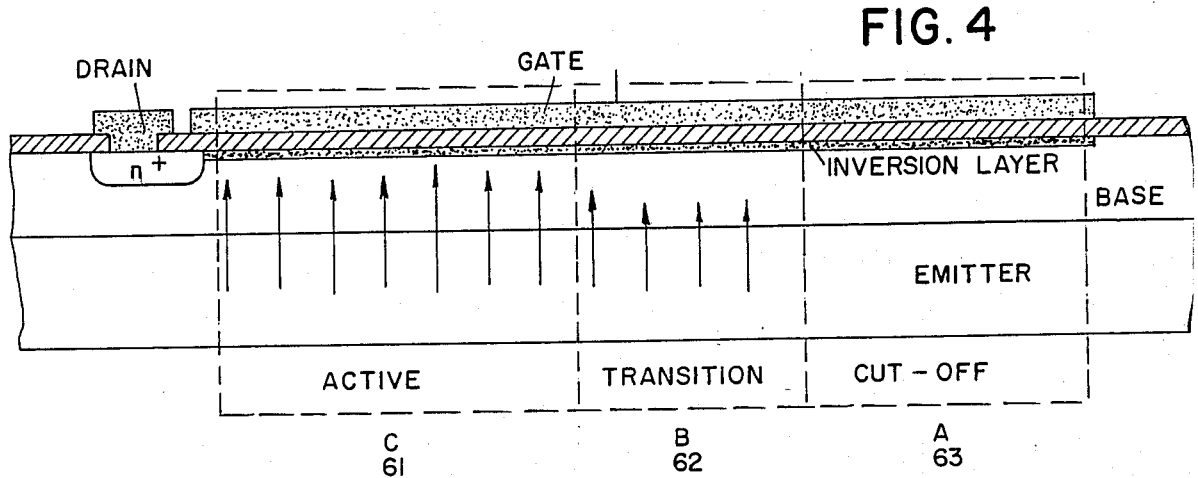
FIG. 4 is a cross-section of the forward active biased MOSBJT with the inversion layer present under partial device cut-off. The arrows indicate the direction of the base minority carrier flux and the length of the arrows represent the relative magnitude of the flux. Also shown are sketches of the base minority carrier profiles for the (a) cut-off (b) transition region, and (c) the active region.
Figure 4A:
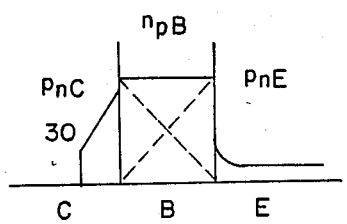
Figure 4B:
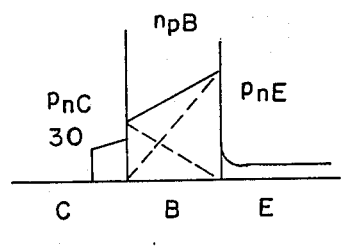
Figure 4C:
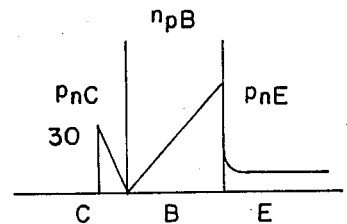
Figure 5:
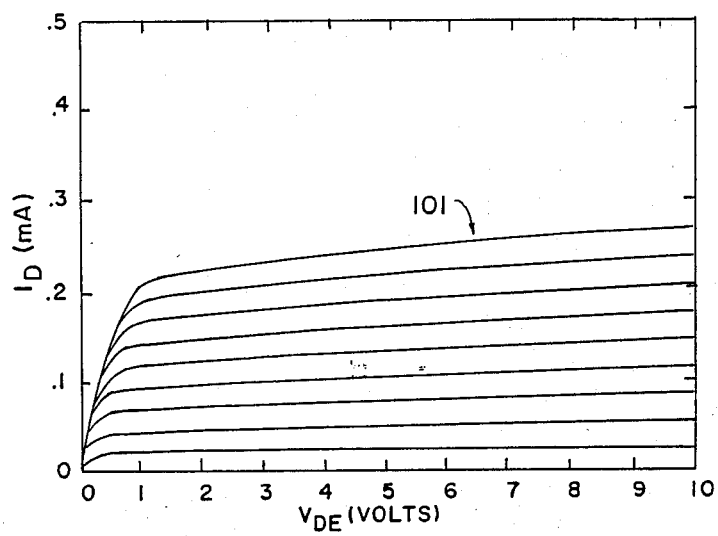
FIG. 5 shows typical large rectangular MOSBJT $I_D$-$V_{DE}$ characteristics. The base currents are in steps of 5 uA from 0 to 45 uA. The gate voltage is 20 V.
Figure 6A:
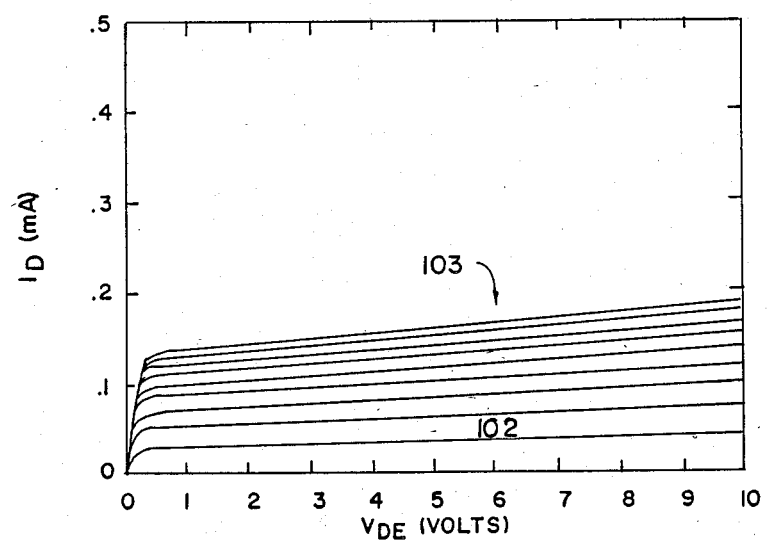
FIG. 6 shows typical large rectangle MOSBJT $I_D V_{DE}$ characteristics. The base currents are in steps of 50 uA from 0 to 450 uA.
Figure 6B:
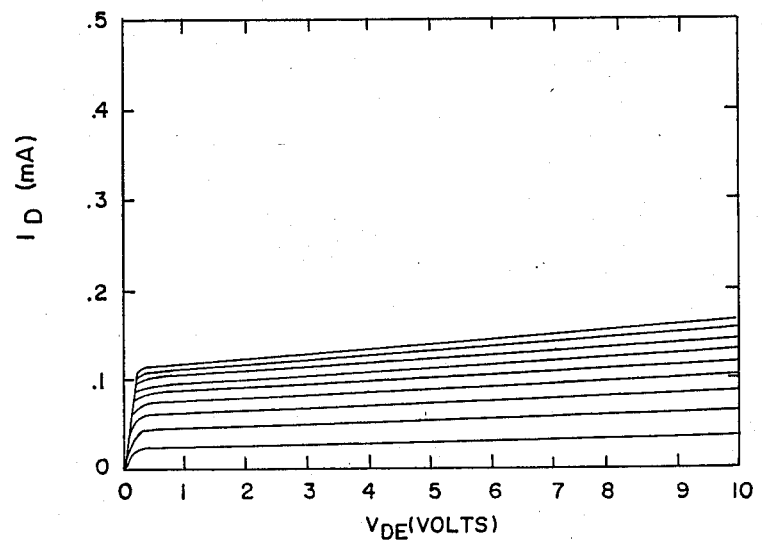
Figure 7:
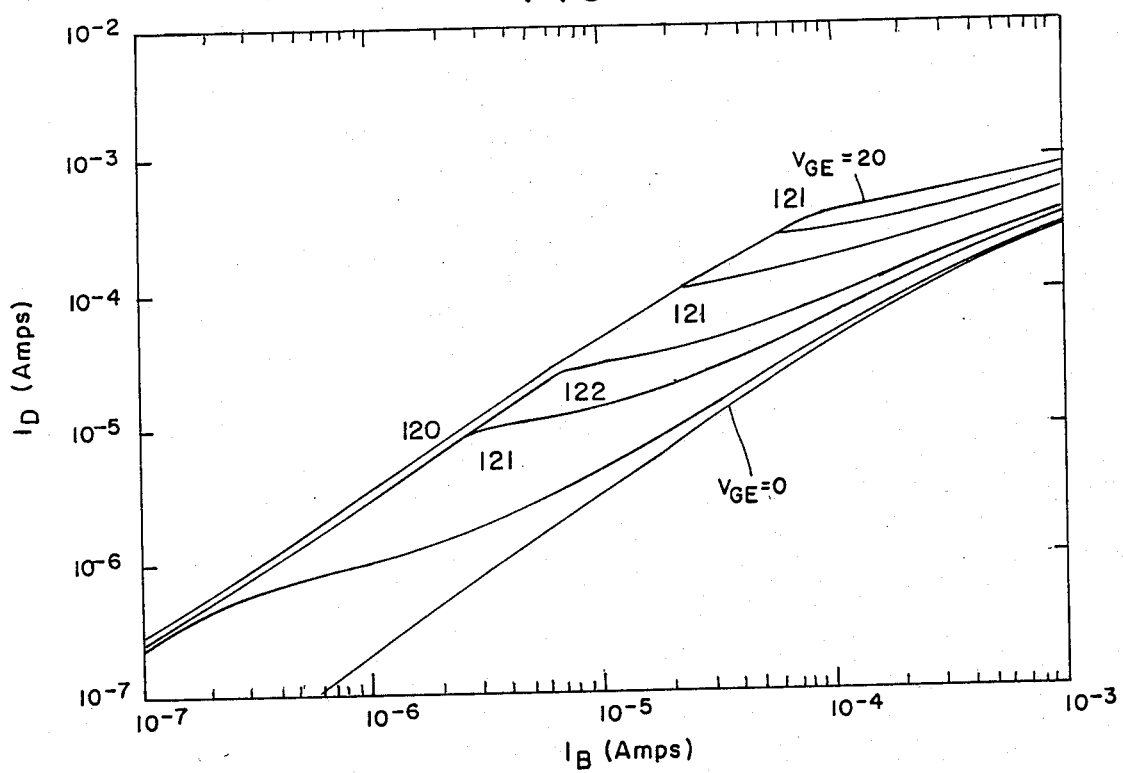
FIG. 7 shows typical quadratic gate MOSBJT $I_D$-$I_B$ characteristics. The gate voltages are 0, 1, 3, 5, 10, 15, and 20 V. $V_{DE}=10$ V.
Figure 8:
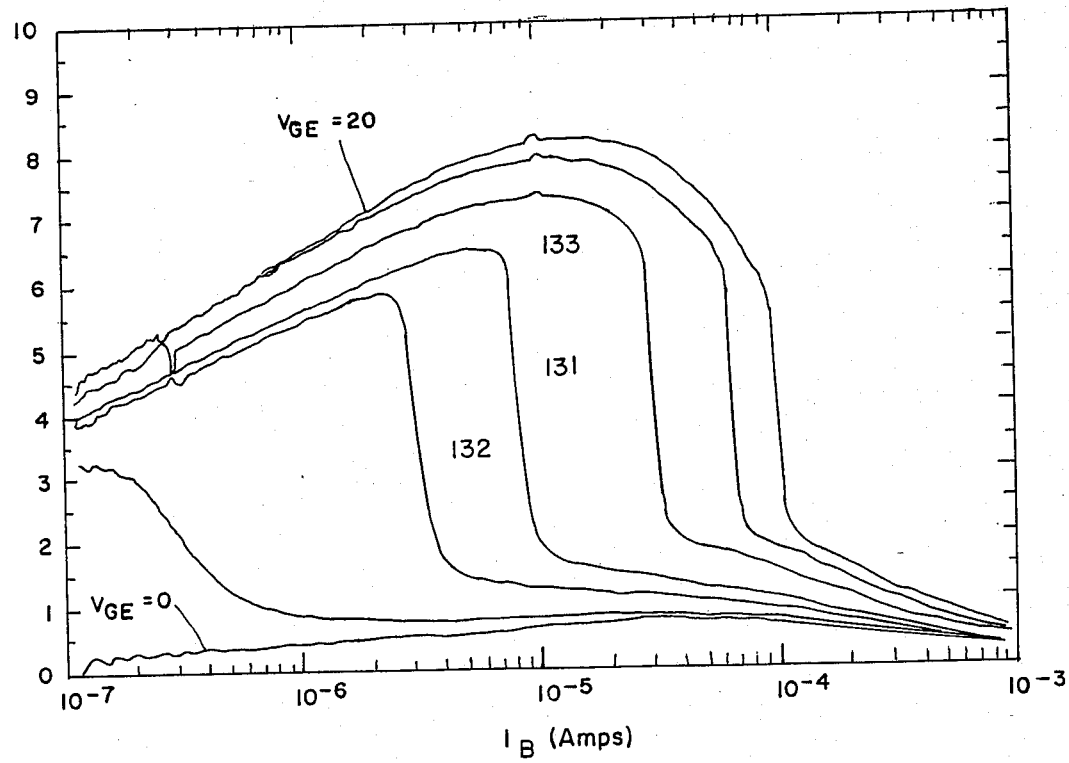
FIG. 8 shows typical triangular gate AC $\beta$-$I_B$ characteristics for $V_{GE}$—0, 1, 3, 5, 10, 15, and 20 volts. $V_{DE}=10$ V.
Figure 9:
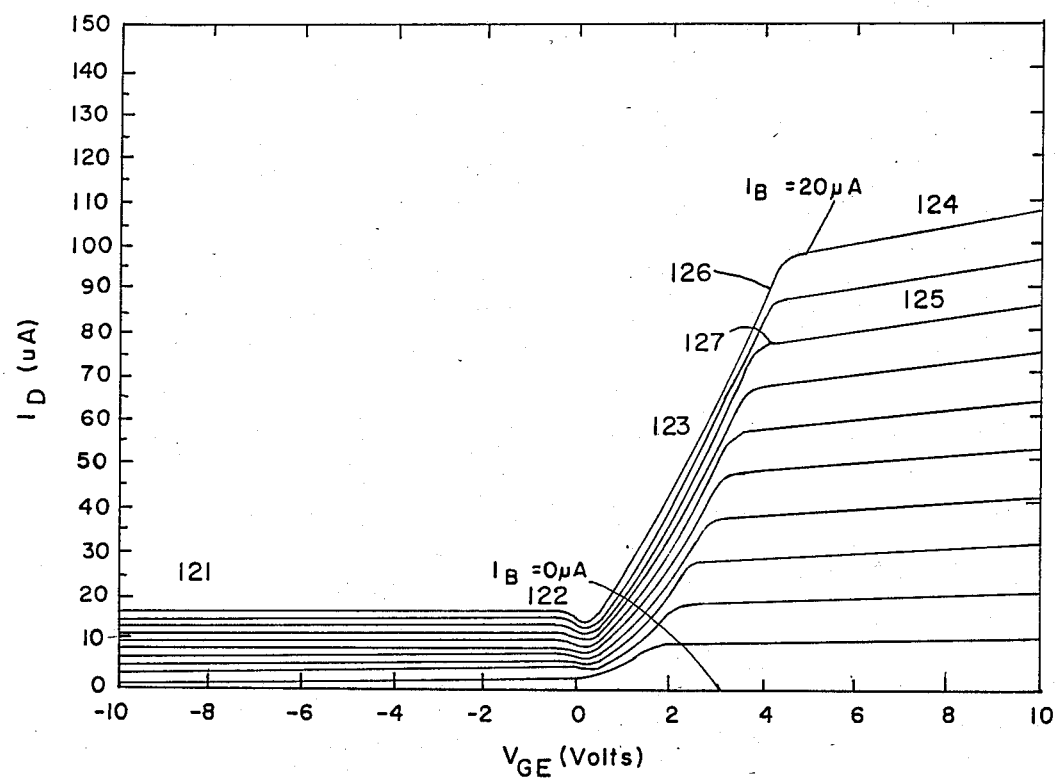
FIG. 9 shows typical large rectangle MOSBJT $I_D$-$V_{GE}$ characteristics. The base currents are in steps of 2 $\mu$A from 0 to 20 $\mu$A. $V_{DE}=10$ V.
Figure 10:
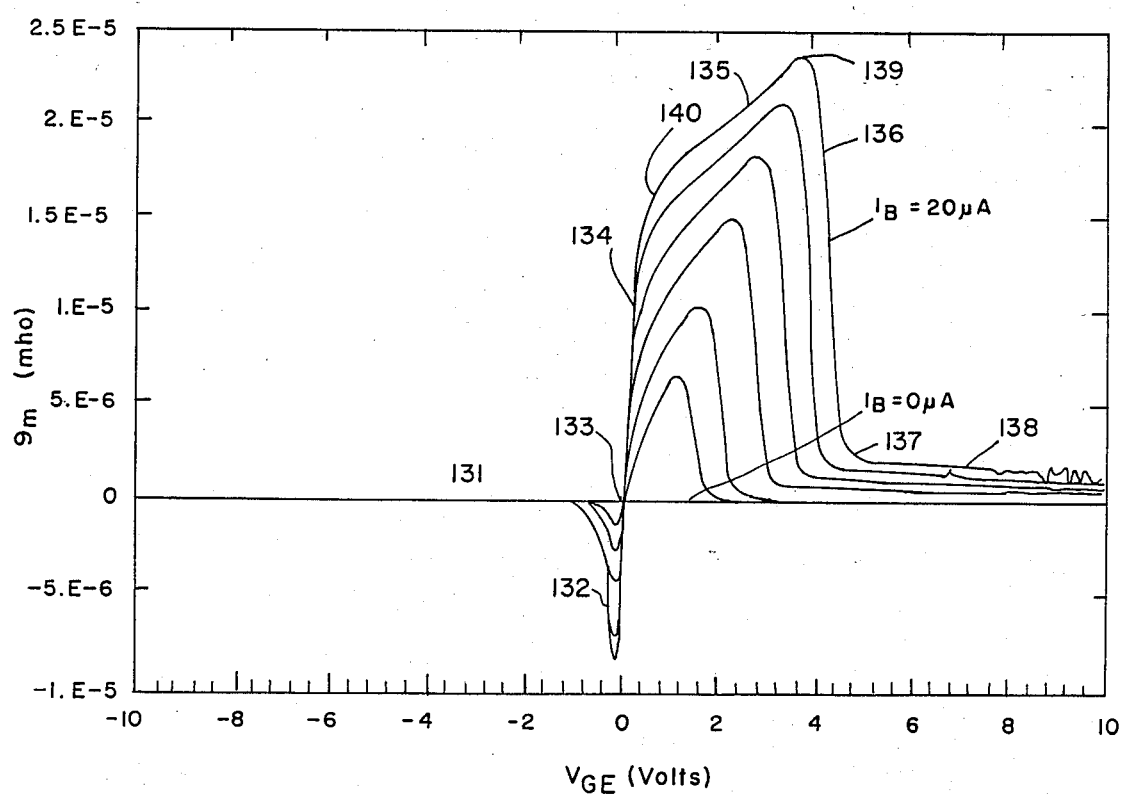
FIG. 10 shows typical large rectangular MOSBJT $g_m$-$V_{GE}$ characteristics. $I_B=0, 2, 4, 8, 12, 16,$ and 20 $\mu$A. $V_{DE}=10$ V.

The invention consists of a four terminal structure (FIG. 1), which can be operated in a variety of ways and constructed in a variety of embodiments. In general, the device consists of four electrical terminals and there are four separate regions which are labeled emitter (1), base (2), channel/collector (3), and gate structure (4) in FIG. 1A and FIG. 1B. The device has a number of embodiments. One such embodiment is shown in FIG. 1, where a channel means 3 located below a gate means 4 and above a doped layer referred to here as base means 2 is located above a layer of a material of another type termed here an emitter means 1. In one method of device operation (FIGS. 2 and 3), the gate means 4 is used to create a resistive n-channel 3 above a lightly doped p-type base 2 which is epitaxially grown on a heavily doped n-type substrate 1. In the embodiment and this particular mode of operation (FIG. 3), a base current is amplified by the normal injection efficiency p-n diode mechanism to inject a large current from the emitter means 1 across the base 2 to be collected by the channel 3. The current flowing along the channel 3 creates a voltage drop along the channel resulting in a non-homogeneous bias along the channel/collector base junction 9 as described above and represented in FIG. 4. The heterogeneous junction bias can result in a distributed and homogeneous forward active and saturation behavior as described above. For low base channel currents and sufficiently strong channel inversion, the channel current is sufficiently low that the entire channel base region remains reverse biased (in this operation mode) and the device shows the normal BJT forward active characteristics (FIG. 5, 101). As the base current $I_B$ is increased, a portion of the device goes into bipolar saturation or cutoff (FIG. 5, 101). That portion of the device in saturation (cutoff) has a larger amount of base recombination current and, for certain ranges of gate voltage, additional base recombination current arising at the semiconductor interface as is well known for gated bipolar structures. In this case, only a small fraction of the total constant base current is leftover for the forward active region and the dc current gain is therefore reduced for this range of gate voltage. The ac gain $b_{AC}$ is reduced even more. As the total base current is increased and the resultant collector channel current increased, the distributed self biasing results in an even larger device area operating under BJT saturation conditions. This reults in a further decrease in $b_{dc}$ and $b_{ac}$. Typical effects are displayed in FIG. 6. At lower base currents, the collector current characteristics are evenly spaced 102. When saturation effects begin, the collector currents at different base currents begin to squeeze together (103) reducing $b_{ac}$ and dramatically reducing $b_{ac}$ with a further increase in the dc base current. The $I_d$ ($-I_c$) characteristics can also be plotted as $I_d(-I_c)$ vs. $I_B$ for different values of gate to emitter voltage $V_{GE}$ as shown in FIG. 7 for a quadratic gate shape. In FIG. 10, the upper straight line region (120) corresponds to a normal BJT operation without any onset of saturation effects. The onset of saturation corresponds to the divergence of the $I_d$ vs. $I_B$ characteristics for the upper straight line as shown for $V_{GE}$- 20V (121). The slope of the curve $dI_C/dI_B$ along the constant $V_{GE}$ curve (122) corresponds to the low frequency AC gain. FIG. 9 shows $dI_C/dI_B$, i.e., $b_{AC}$ vs. $I_{BO}$, for a triangular gate device ($I_{BO}$ is the dc base current).

The steepness (131) of $b_{AC}$ vs. $I_{BO}$ (FIG. 9) at the onset of saturation effects provides a sensitive method of chemical sensing. If a chemically sensitive gate is used, a small shift $DV_{TH}$ in the MOS threshold voltage ($V_{TH}$) results in a small shift in the particular $V_{GE}$ characteristic. By biasing the device at the value of $I_{BO}$ where the steepest value of $b_{AC}$ (132) occurs, the shift in $b_{AC}$ at this value of $I_{BO}$ provides a sensitive measure of the chemically induced shift of the threshold voltage. The device sensitivity is, in this case, directly proportional to the large slope of $b_{AC}$ vs. $I_{BO}$. A suitable choice of gate shape can be used to select the sensitivity, i.e., to determine $dB_{AC}/dI_B$ vs. $I_{BO}$. For example, a gate which is wide at the drain/collector contact and narrow at the opposite end of the channel will have a $b_{AC}$ which decreases more slowly with $I_{BO}$ than a gate which has the same shape, but with the narrow end at the drain/collector contact.

An alternative method of sensing the effect of the shift in the $b_{AC}$ vs. $I_B$ curve is to fix $V_{GE}$ and fix $b_{AC}$, e.g., by controlling the dc current $I_{c(=Id)}$ or $I_{bo}$ and applying a fixed AC base current $I_{BAC}$ sinlt and sensing the output AC collector current $I_{CAC}$ sinlt. $I_{BO}$ is then adjusted until the same $I_{CAC}$ sinlt is measured at the drain/collector contact. The shift in $I_{BO}$ for a fixed $V_{GE}$ and $b_{AC}$ provides sensitive information on the effect of the chemically altered MOS threshold $V_{TH}$. For this sensing mode, a BJT structure with a current gain b <<1 increases the device chemical sensitivity and resolution of $DV_{TH}$ due to the presence of the chemical species.

An alternative method of sensing is to create a buried channel and before the chemical is present, sweep $I_{BO}$ to locate the value at which saturation effects begin. $I_{BOK}$ (133), the value of $I_{BO}$ at the knee, representing the onset of saturation effects is measured; the same process is repeated after the measured chemical is absorbed and the new value $I_{BOK}$ provides a measure of the sensed chemical. For the buried channel device, the method of measuring the shift in bac can also be used. For the buried channel device, no gate voltage need be applied and the gate itself may be the chemically active material. Alternatively, if no MIS structure is used, the buried channel surface (semiconductor surface) can be used as the active chemically sensitive material. In the later case, when the base surface is exposed to the chemical, and when the surface recombination velocity is affected by the exposed surface, another sensing method can be used. Here, the amount of surface recombination base current is altered by the absorbed chemical resulting in a change in the slope of $b_{AC}$ vs. $I_B$. The sensitivity can be affected by choosing the gate shape which will result in the largest change in $b_{AC}(I_{BO})$ with a small chemically induced change in the surface recombination velocity.

An alternative method of interrogating the device in order to sense a chemically altered gate threshold voltage is to use the transconductance $g_m$ vs. gate to emitter voltage $V_{GE}$ characteristic. FIG. 9 shows $I_D$ (-$I_C$) vs. $V_{GE}$ for various values of $I_B$. Differentiating the characteristics in FIG. 9 results in the $g_m$ vs. $V_{GE}$ characteristics shown in FIG. 10. There are several prominent features in FIG. 10 which can be exploited for very sensitive chemical sensing. The $I_D$ vs. $V_{GE}$ characteristics for different values of $I_{BO}$ can be understood in the following way. For sufficiently large negative values of $V_{GE}$ in FIG. 9, the channel below the gate is in enhancement and only the parasitic BJT under the collector/drain contact nipple is operating as a BJT. The rest of the device shows base recombination current without amplification when the region under the gate is under strong enhancement. The large recombination in the base region draws a large portion of the applied constant base current resulting in small DC and AC current gains. This is illustrated by the small separation in $I_D$ for changes in $I_{BO}$ (121). As $V_{GE}$ is decreased, the device eventually begins to move out of enhancement and the Fermi level sweeps through the band gap at the surface. This allows recombination at the surface to occur via surface states and an even larger fraction of the base current goes into recombination, further reducing the gain and therefore $I_D$ as shown (122). As the channel begins to become biased into weak inversion, the surface recombination velocity again decreases and the channel also begins to collect current originating from the emitter (123). The degree of channel biasing and the onset of saturation effects is directly dependent on the base current magnitude $I_{BO}$. Thus, the curvature of the dip (122), the slope of the rise (123) and the value of $V_{GE}$ at the knee (126, 127) are all dependent on $I_{BO}$ and $V_{GE}$. For very strong inversion, such that no BJT saturation behavior occurs in any part of the channel, the normal BJT forward active behavior is observed (124, 125).

The transconductance $g_m$ (-$dI_D/dI_B$) is shown in FIG. 10. It is observed here that there is a base current dependent negative transconductance region (132), and a value of $V_{GE}$ where $g_m = 0$ (133) and which is invariant with $I_{BO}$. This value of $V_{GE}$ is termed $V_{THG}$ here and identifies a base current invariant transconductance threshold voltage useful for chemical sensing applications. The value of $V_{THG}$ depends upon the thickness of the gate oxide and the doping of the substrate beneath the gate oxide. There is also a steep onset of positive values of $g_m$ ($V_{GE}$) dependent upon $I_{BO}$. This region is followed by a lower slope region (135) where the magnitude of $g_m$ and its slope are dependent upon the value of $I_{BO}$ followed by a drop in $g_m$ ($V_{GE}$) (136). The onset of the later drop (139) and the value of $V_{GE}$ at which $g_m$ becomes essentially independent of $V_{GE}$ (137) are all dependent on $I_{BO}$ and $V_{TH}$ (and $V_{THG}$) and thus are suitable parameters for chemical sensing applications.

Various features of the $g_m$ vs. $V_{GE}$ characteristics can be used for sensing. Of particular use is the time invariant value of $V_{GE}$ where $g_m = 0$, i.e., $V_{GE} = V_{GTH}$ (133). This is a very precide threshold voltage which is invariant with $I_{BO}$ and at which $g_m$ vs. $V_{GE}$ is approximately a straight line. $V_{THG}$ will shift due to chemical effects and $V_{THG}$ is easily measured with great accuracy using a null measurement. The amplification of a small AC voltage to the gate results in an AC current which is negative to the left of $V_{THG}$ (133), positive to the right of $V_{THG}$ and zero at $V_{THG}$. Use of a simple feedback circuit, known to those skilled in the circuits art, can be used to adjust a DC voltage feedback to $V_{GE}$ to achieve an AC current null with great accuracy. A measure of $V_{GE}$ at $I_{AC}$ - 0 provides $V_{THG}$. If $V_{TH}$ (MOS threshold) shifts due to an absorbed chemical species at the gate, $V_{THG}$ shifts precisely by the same amount. This chemically induced shift in $V_{THG}$ is easily and precisely measured by measuring $V_{THG}$ and thus the absorbed chemical is sensed. $V_{THG}$ is much easier to accurately determine than $V_{TH}$. This is a very accurate sensing method since it uses a null measurement. When $g_m = 0$ (133) occurs, the device is behaving as a gated emitter collector device.. (Similarly, a gate emitter BJT device can be used and here gm=0 also accurately identifies a very sensitive threshold voltage $V_{THG2}$).

At $g_m = 0$, it can be shown that the linear behavior of $g_m$ ($V_{GE}$) can be expressed as $g_m$=const. $\times \beta_{THG} I_{BO} S_o (V_{GE} V_{THG})$ where $\beta_{THG}$ is the current gain at transconductance threshold voltage (at $g_m = 0$) and where $S_o$ is the maximum value of the gate voltage dependent surface recombination.

The device can be designed with increased sensitivity by choosing a large DC current gain, the method of which is known to those skilled in BJT art. A large value of $S_o$ consistent with a large value of $\beta_{THG}$. By operating at a large collector current ($I_C = I_{BO} \times \beta_{THG}$) at $V_{THG}$, the resolution of $V_{THG}$ is improved so long as IR drops from the base contact are negligible. (This latter condition is a non-obvious design constraint for a maximum sensitivity device.)

To the right of $V_{THG}$ in FIG. 10, the distributed character of the device influences the device's electrical characteristics. Here the slope at 134, 135, 136 and the position and shape of the knees (139 and 140) are dependent upon the chemically altered threshold voltage.

Figure 11:
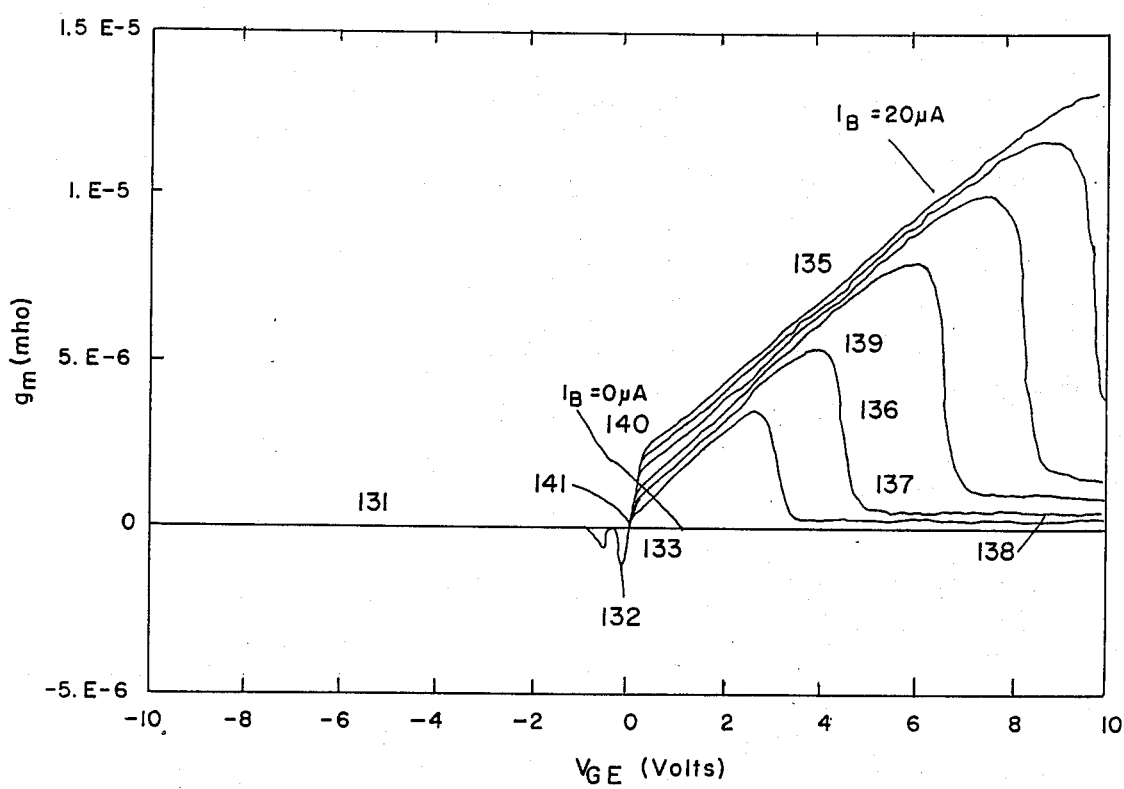
FIG. 11 shows typical cubic MOSBJT $g_m$-$V_{GE}$ characteristics. $I_B=0, 2, 4, 8, 12, 16,$ and 20 $\mu$A. $V_{DE}=10$ V.

FIG. 11 shows results similar to those in FIG. 10, but where the gate shape is now cubic instead of rectangular as it is for the device of FIG. 10. Gate shape can clearly be used to affect the sensitivty of the various parameters suitable for sensing interrogation. The effect of gate shape is to affect the resistance per unit length of the channel and the amount of surface recombination. In FIG. 11, the presence of structure (141) in $g_m$ vs. $V_{GE}$ is due to surface state charging and this alos can be used to define a precise threshold voltage and this too is claimed here for chemical sensing applications.

Figure 12A:
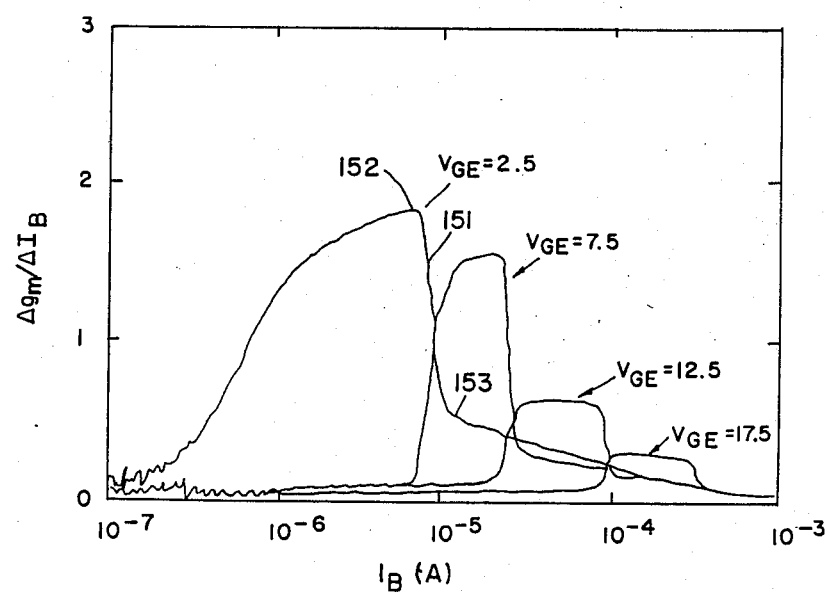
FIG. 12 is $\Delta g_m/\Delta I_B$ versus gate voltage for a typical MOSBJT. The gate voltages are 2.5, 7.5, 12.5, and 17.5. $V_{DE}=10$ V.
Figure 12B:
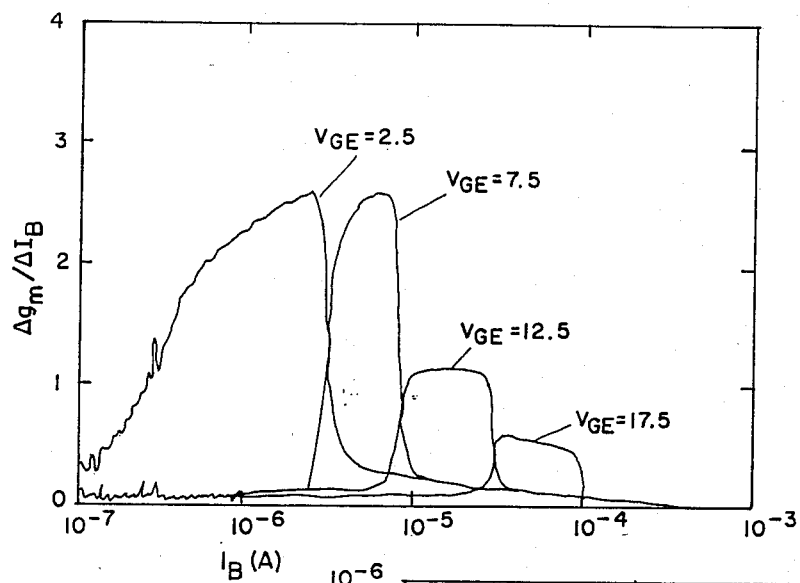

The electrical characteristic of $dg_m/dI_B$ vs. $I_{BO}$ can also be used for sensing purposes. FIG. 12 shows such characteristics for various fixed values of $V_{GE}$. A shift in $V_{TH}$ due to an absorbed chemical will result in a shift in the characteristics. By biasing the device at $I_{BO}$ such that $dg_m/dI_B$ is a maximum and then inspecting the change in $dg_m/dI_B$ due to a chemically induced shift in $V_{TH}$, the chemical presence and magnitude of the absorption can be determined. Alternatively, $dg_m/dI_B$ can be fixed and the shift in $I_{BO}$ to give the same value of $dg_m/dI_B$ can be measured to determine the strength of the chemical absorbed. The peak position can also be used as the sensed parameter. The method for the above described sensing approach is to apply an ac base current and ac gate voltage as well as the dc values and to inspect the ac components.

The strong non-linearity such as those at 152 and 153 in FIG. 12 or 137, 139, or 140 in FIG. 11 can be used to sense chemical absorption. By applying small ac signals and observing the harmonics or mixing strength, the position of the strongest non-linearities may be accurately determined. These positions shift with a shift in $V_{TH}$.

Figure 13:
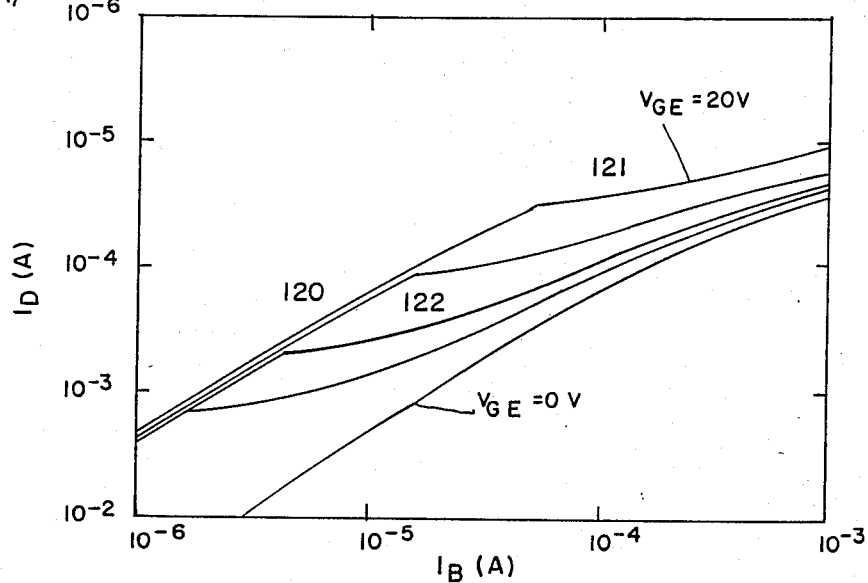
FIG. 13 shows typical cubic MOSBJT drain current, as a function of base current. $V_{GE}=0, 3, 5, 10,$ and 20 V. $V_{DE}=10$ V.
Figure 14:
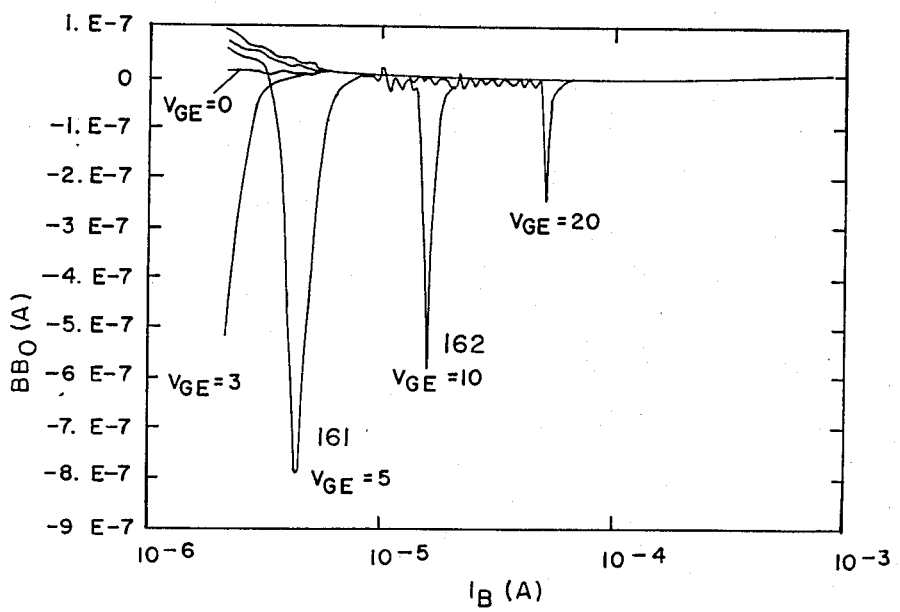
FIG. 14 shows typical cubic MOSBJT empirical dc Fourier coefficient, as a function of base current. $V_{GE}$—0, 3, 5, 10 and 20 V. $V_{DE}=10$ V.

FIGS. 13, 14, 15 and 16 show typical $I_d$ vs. $I_{BO}$ characteristics for the MOSBJT device embodiment. FIG. 13 shows typical gate $I_d$ vs. $I_B$ characteristics. FIG. 14 shows the small signal zero order (DC), i.e., rectified, drain current output BBo for a small AC base current, $I_{B1}$ sinωt, added to $I_{BO}$. The effects of the onset of BJT saturation correspond to the peak value of $\beta\beta_0$ (161,162). A chemically induced shift in $V_{TH}$ shifts all of the knees (121) equally. This shift can be determined by measuring the peak shift corresponding to 161, 162, etc., in FIG. 14.

Figure 15:
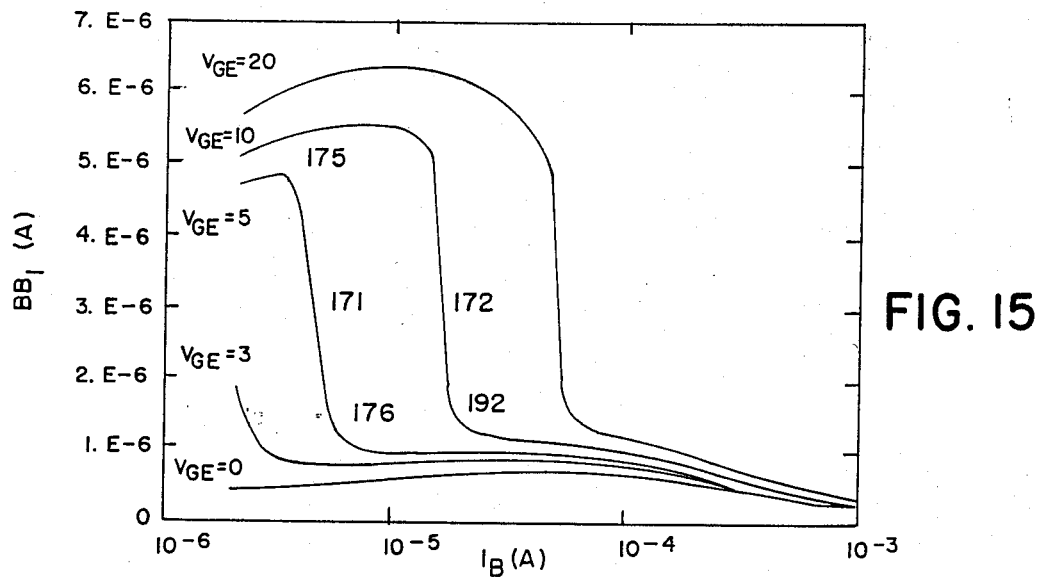
FIG. 15 shows typical cubic MOSBJT empirical fundamental Fourier coefficient as a function of base current. $V_{GE}$=0, 3, 5, 10, and 20 V. $V_{DE}$=10 V.
Figure 16:
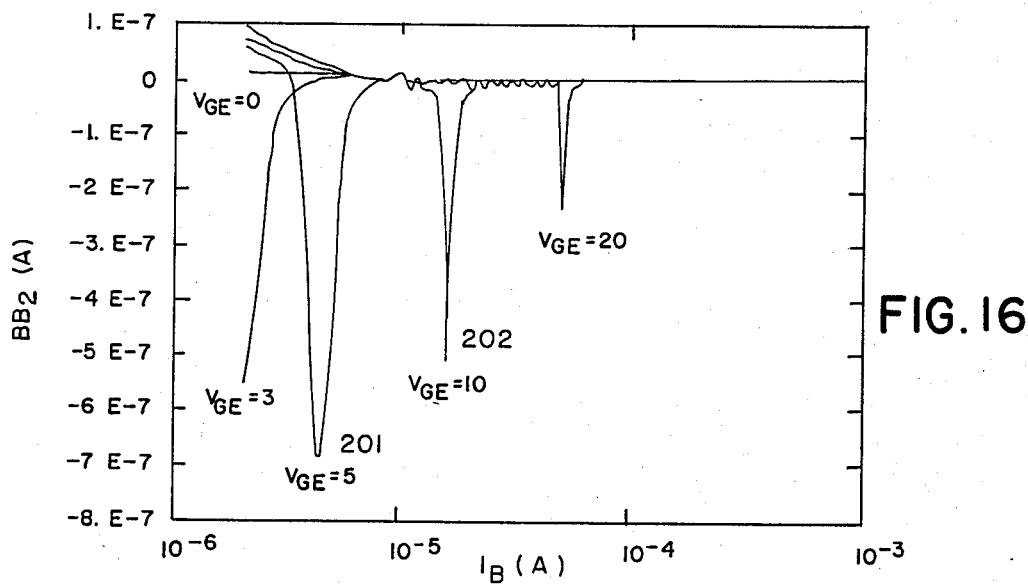
FIG. 16 shows typical cubic MOSBJT empirical first harmonic Fourier coefficient as a function of base current. $V_{GE}$=0, 3, 5, 10, and 20 V. $V_{DE}$=10 V.

The fundamental of $I_d$, i.e., $I_{d1}$ sinωt is identified as BB1 in FIG. 15. Using methods similar to those described above for steep characteristics, i.e., for large slopes (171,172), a small shift in $V_{TH}$ due to an absorbed chemical can be very accurately determined by either fixing BB1 and measuring the new value of $I_{BO}$ for fixed applied $V_{GE}$, or by fixing $I_{BO}$ and measuring the change in BB1. BB2 in FIG. 16 is the first harmonic, i.e., $I_{d2}$ sin2wt. The knees (175 and 176) in FIG. 15 result in the peaks in FIG. 16. A shift in the peak location in FIG. 16 (201, 202) can be used as the sensed parameter which changes with chemisorption modification of $V_{TH}$.

Figure 17:
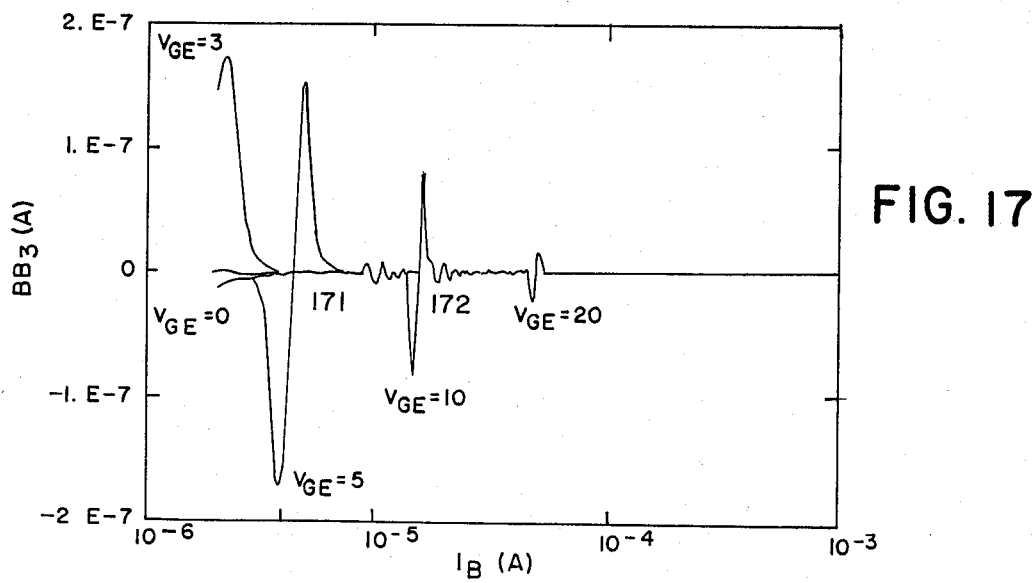
FIG. 17 shows typical cubic MOSBJT empirical second harmonic Fourier coefficient as a function of base current. $V_{GE}$ =0, 3, 5, 10, and 20 V. $V_{DE}$=10 v.
Figure 18:
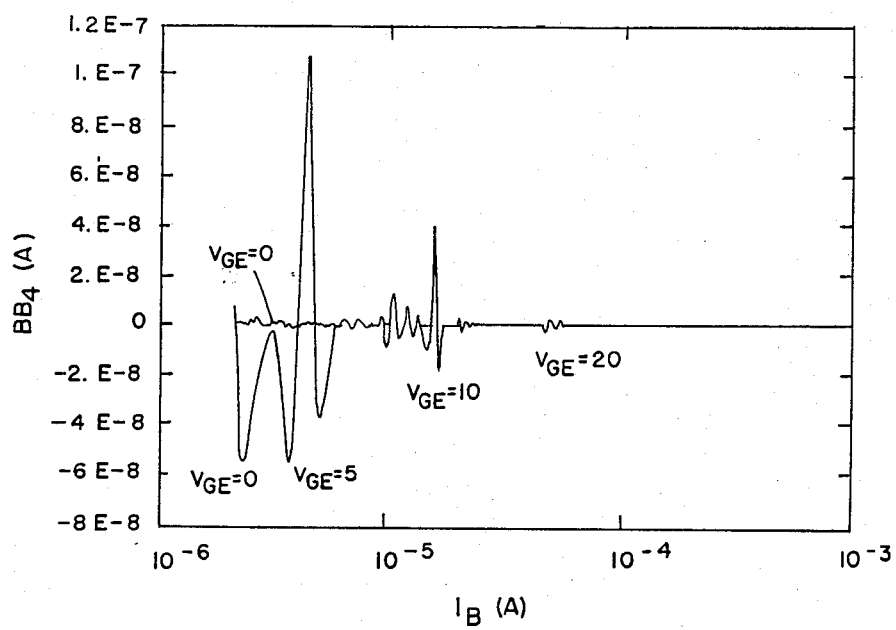
FIG. 18 shows typical cubic MOSBJT empirical third harmonic Fourier coefficient as a function of base current. $V_{GE}$=0, 3, 5, 10, and 20 V. $V_{DE}$=10 V.
Figure 19:
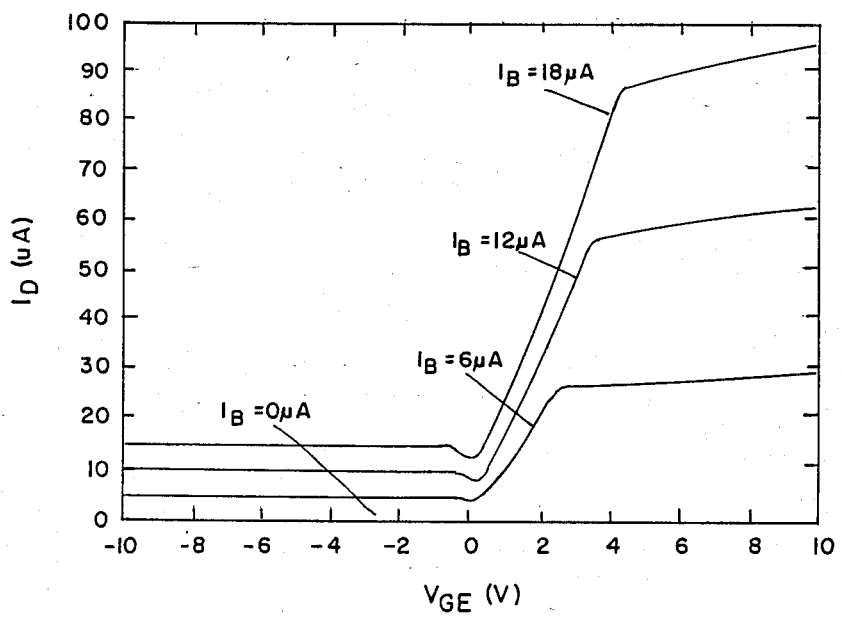
FIG. 19 shows typical large rectangle MOSBJT drain current as a function of gate voltage. $I_B$=0, 6, 12, and 18 μA. $V_{DE}$=10 V.
Figure 20:
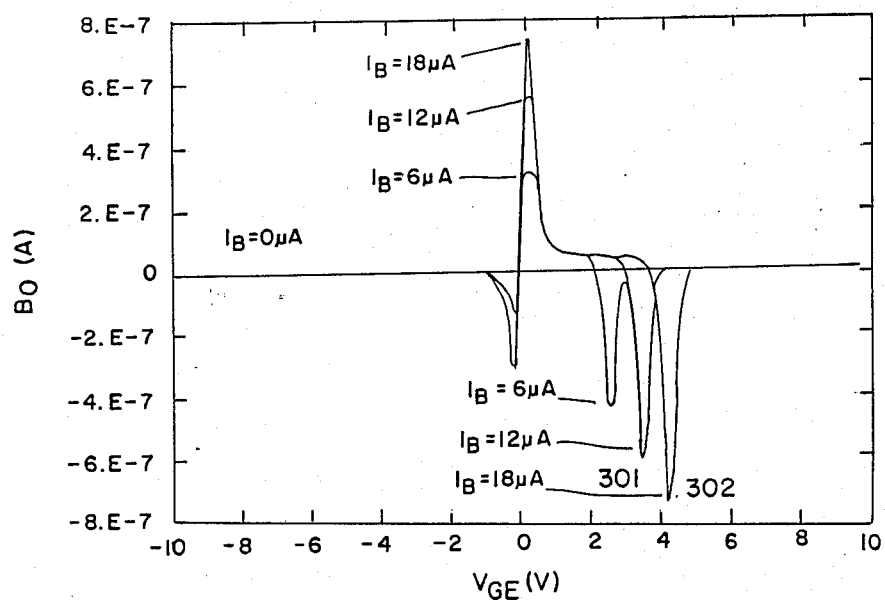
FIG. 20 shows typical large rectangle MOSBJT empirical dc Fourier coefficients as a function of gate voltage. $I_B$=0, 6, 12, and 18 μA. $V_{DE}$=10 V.
Figure 21:
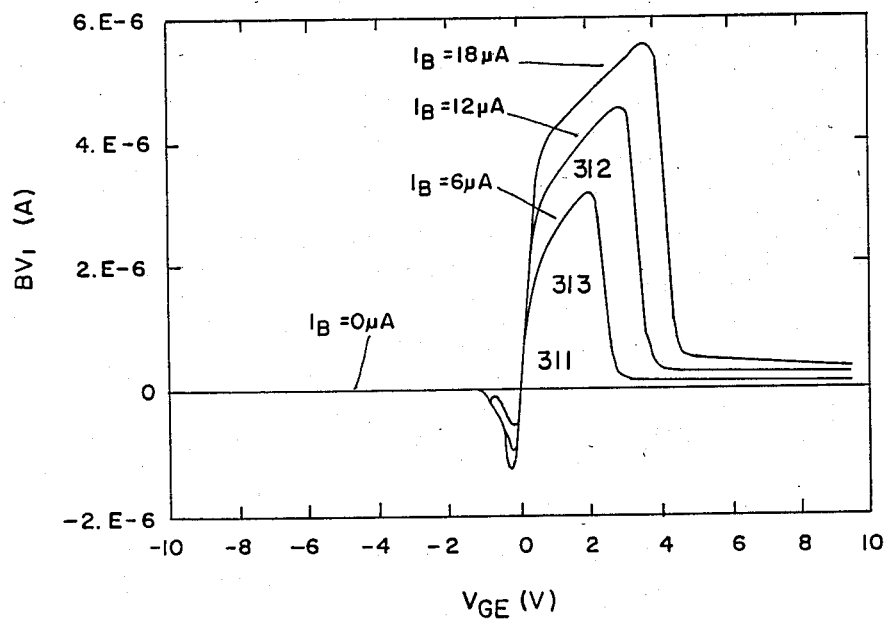
FIG. 21 shows typical large rectangle MOSBJT empirical fundamental Fourier coefficients as function of gate voltage. $I_B$=0, 6, 12, and 18 μA. $V_{DE}$=10 V.
Figure 22:
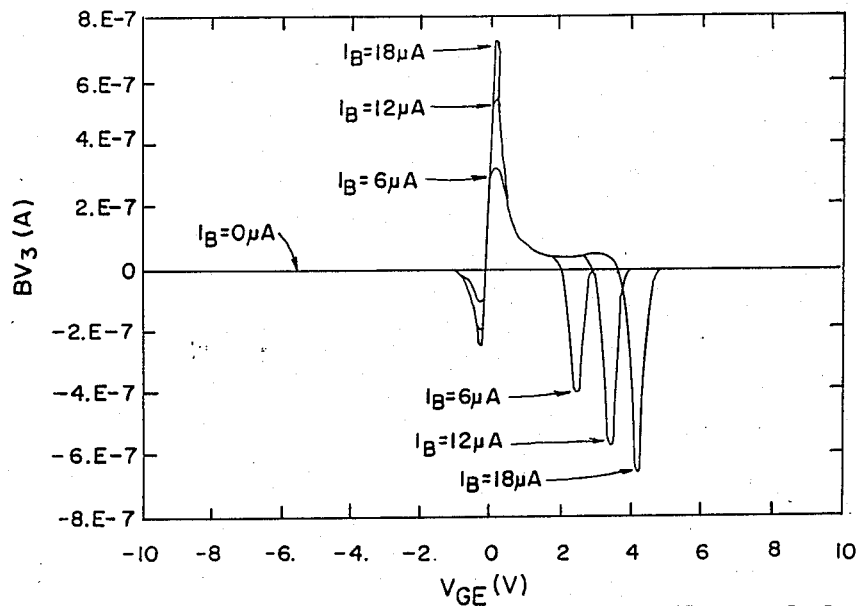

FIGS. 17 and 18 show the related second and third related harmonic components. The crossovers 171, 172) in FIG. 17 are at precise values of $I_{BO}$ and these shift with a chemically induced threshold voltage shift and can be accurately determined.

Similar characteristics can be acquired from the device output for an applied AC gate voltage superimposed on the DC gate voltage. FIGS. 19 to 22 show zero order $BV_o$ (DC, i.e., rectification) through third harmonic $BV_4$ vs. $V_{GE}$ for various fixed values of $I_{BO}$. The positions of the peaks, values of slopes, etc., can be used for chemical and other sensing in a manner similar to the other methods described above and with the above explanations. These and other methods using harmonics, mixing, etc., will be obvious to those skilled in the art. And, other characteristics of the four terminal device and their uses in sensing and electronics will also be obvious to those skilled in the art after reading the above.

The use of a JFET conducting channel or MESFET conducting channel or epitaxial buried channel or buried channel or such channel without a protective oxide or coated with a chemically sensitive layer or an interface together with a distributed BJT where the channel functions as a distributed collector or distributed emitter will likewise be obvious to those skilled in the art after reading the description of the distributed channel bipolar device. The use of similar zero value (null) parameter threshold voltages or current thresholds to measure chemically induced shifts will also be obvious to those skilled in the art after reading the above descriptions. All of these approaches as well as other related approaches to chemical sensing and other sensing are intended to be covered by the following claims, as are similar structures of non-semiconductor materials. Heterostructures of similar nature as those devices described above and employed in any of the above or similar manners are also intended to be covered by the above descriptions and by the following claims.

Devices similar to those above but where the threshold voltage or conductance of the channel is affected by an externally applied quantity which changes any of the threshold voltages or changes the channel conductance are also intended to be included here.

Such sensing applications are intended to include the effects of force or pressure which affect the position of recombination centers in the band gap or channel resistivity or threshold voltage and to also include the effects of optical absorption in altering channel conductance, as well as photoFET and photoBJT effects and in altering the occupied trap densities which relate to various threshold voltaes including $V_{TH}$, $V_{THG}$ and $V_{THG2}$. Magnetic and acoustic sensing uses of the devices are also included. For example, an applied magnetic field will create a channel magnetoresistance which can dramatically affect the device characteristics. All of these and other sensing applications are intended to be covered by the present application.

Non-sensing electronic applications are also intended to be covered by the above explanations and embodiments and descriptions and claims included herein. Useful electronic functions of the device include, but are not limited to, the presence of a reference voltage $V_{THG}$ useful in circuit applications, harmonic generation and mixing, a current controlled and voltage controlled AC and DC gains, voltage and current controlled transconductance, etc. Also claimed is the use of gate geometry as a useful design feature to meaningfully affect device parameters of interest, including the use of embodiments and geometries of the devices which provide useful power relationships (dependences) between parameters, such as base current for arithmetic and other functions in discrete and integrated circuits.

Also claimed is the use of the active and saturated region of the device for amplification of various waves including optical, electromagnetic (such as millimeter waves) and acoustic waves.

Various embodiments and fabrication procedures for this device can be imagined. In the preferred embodiment, the device has an MOS structure and related channel structures located over a base which is placed over a heavily doped substrate. That is, the distributed channel BJT device described above where the gate means is an MOS structure, the base means is a p-epi or diffused layer and the emitter means is a heavily doped n-type substrate in the preferred embodiment of the device.

The distributed channel BJT device can be fabricated in the following manner. A heavily doped As doped (n+) silicon substrate of 0.005Ωcm is selected and a 1

Ωcm boron doped (p) epi-layer of 5 μm thickness is grown on the AS doped substrate. A protective SiO2 layer is grown on the epi-layer in a manner well known to those skilled in the art. An n+ contact region is then diffused into the epi-layer through a window which has been opened using standard photolithographic etching and diffusion techniques as is well known to those skilled in the art.

Figure 23:
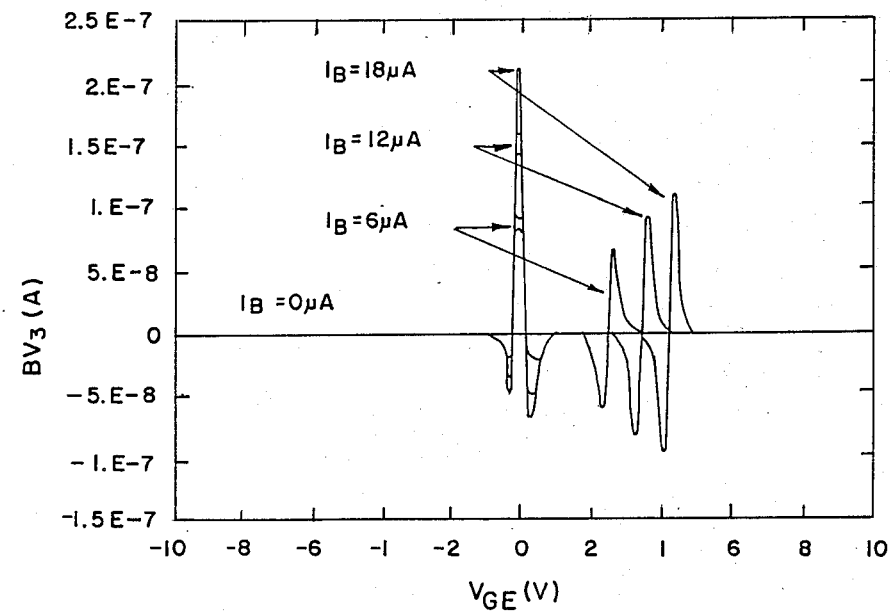
FIG. 23 shows typical large rectangle MOSBJT empirical second harmonic Fourier coefficients as function of gate voltage. $I_B$=0, 6, 12, and 18 μA. $V_{DE}$=10 V.
Figure 24:
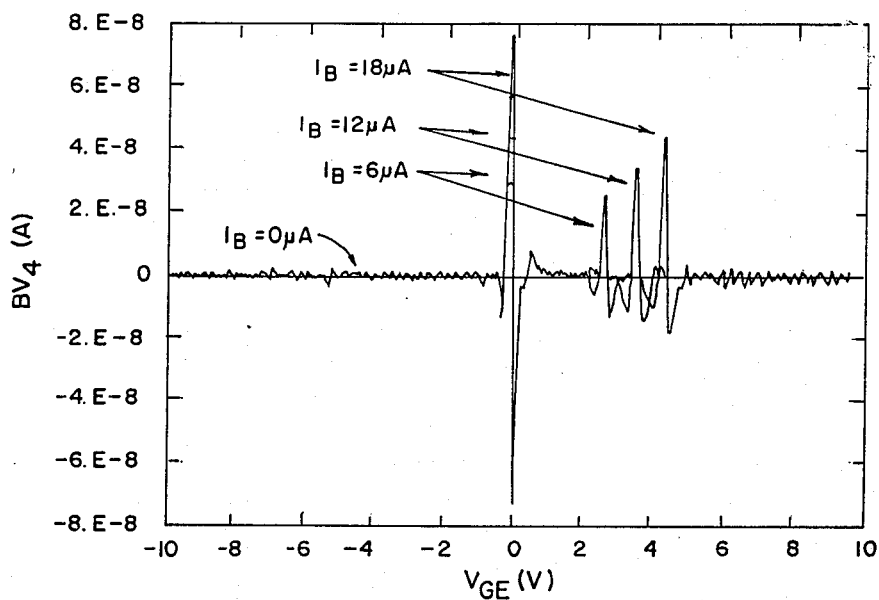
FIG. 24 shows typical large rectangle MOSBJT empirical third harmonic Fourier coefficient as function of gate voltage. $I_B$=0, 6, 12, and 18 μA. $V_{DE}$=10 V.
Figure 25A:
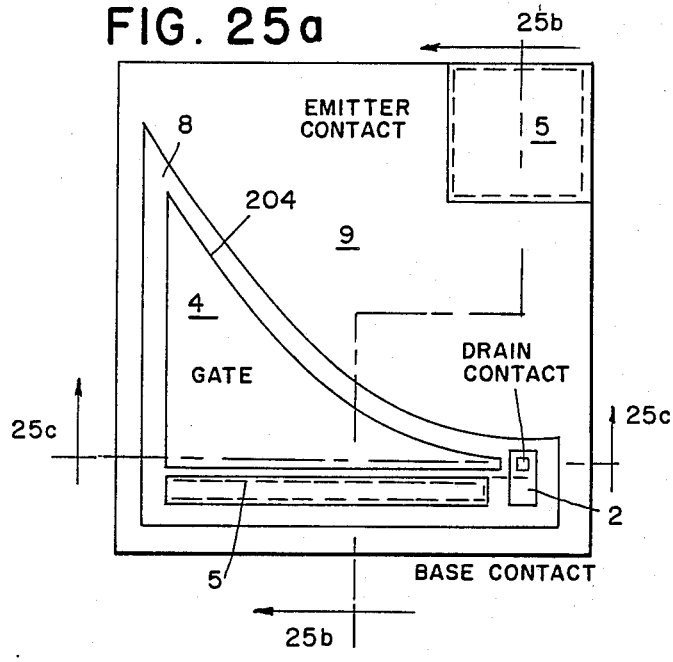
FIG. 25 is a top view (showing dimensions) and cross-sections of a MOSBJT with a quadratic shaped gate.
Figure 25B:
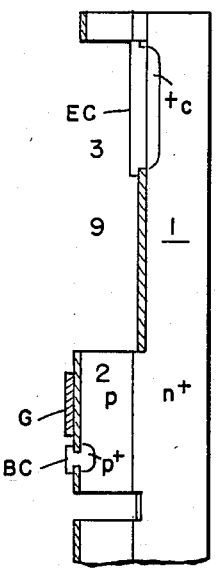
Figure 25C:
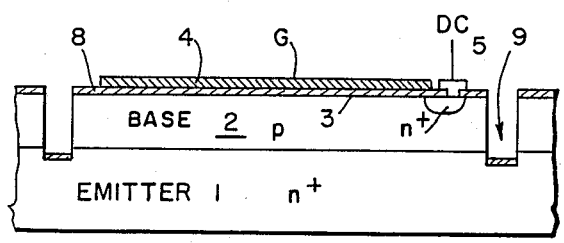

The appropriate gate material (which may be chemically sensitive, such as carbon or a-Si or another material such as aluminum) is deposited on the oxide, the gate region patterned and the device mesa etched using standard silicon technology and procedures well known to those skilled in the art. A top view of such a device, showing dimensions, is illustrated in FIG. 23. The gate (4), base (2), emitter (1), mesa (trench) isolation trench (9) used to confine the emitter injection, gate oxide (8), drain contact (5) are all shown for a gate where the curved edge (204) is a cubic curve.

Figure 26:
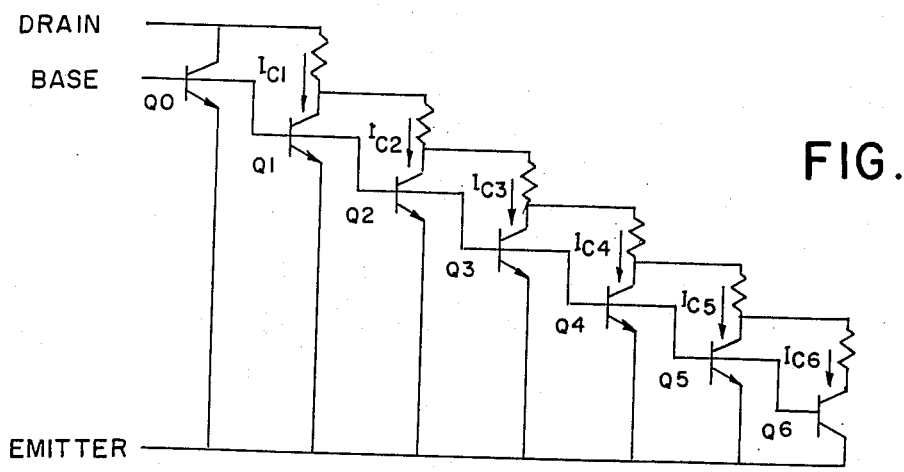
FIG. 26 is a simplified one-dimensional multi-lump model for the forward active biased MOSBJT. Fixed resistances are substituted for the MOSFETS of the one-dimensional multi-lump MOSBJT.
Figure 27:
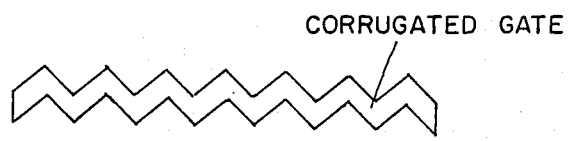
Figure 28:
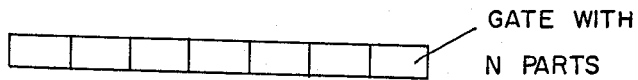

The distributed character of the distributed channel BJT in the embodiment with the channel as collector is represented by the distributed equivalent circuit shown in FIG. 26. The larger the number of elements, the more accurate will be the model for the distributed MOSBJT.

The disclosure of the invention described herein represents the preferred embodiment of the invention. However, variations thereof, in the form, construction, arrangement of various electronic parts and biases and use of various electrical characteristics thereof and modified applications of the invention are possible without departing from the spirit and the scope of the appended claims.

| LIST OF SYMBOLS | |
|---|---|
| MOSFET | METAL OXIDE SEMICONDUCTOR FIELD EFFECT TRANSISTOR |
| BJT | BIPOLAR JUNCTION TRANSISTOR |
| MESFET | METAL SEMICONDUCTOR FIELD EFFECT TRANSISTOR |
| JFET | JUNCTION FIELD EFFECT TRANSISTOR |
| IC | INTEGRATED CIRCUIT |
| $V_g$ | VALUE OF GATE VOLTAGE |
| $V_{THG}$ | VALUE OF THE GATE VOLTAGE WHERE THE FET TRANSCONDUCTOR GOES TO ZERO WHEN THE CHANNEL AND DRAIN REGION ARE OPERATED AS A COLLECTOR |
| $V_{THG2}$ | VALUE OF THE GATE VOLTAGE WHERE THE TRANSCONDUCTANCE FOR THE DISTRIBUTED CHANNEL BJT GOES TO ZERO WHEN THE CHANNEL AND DRAIN REGION ARE OPERATED AS AN EMITTER. |
| $V_{TH}$ | NORMAL MOS THRESHOLD VOLTAGE |
| $g_m$ | FET TRANSCONDUCTANCE |
| $I_B$ | VALUE OF THE BASE CURRENT |
| $I_{BO}$ | DC VALUE OF THE BASE CURRENT |
| SUBSCRIPT$_O$ | IDENTIFIES DC VALUE |
| SUBSCRIPT$_{AC}$ | IDENTIFIES AC VALUE |
| SUBSCRIPT$_1$ | USED TO INDICATE AC VALUE |
| $I_{BAC}$ | AC BASE CURRENT VALUE |
| $I_C, I_{CO}, I_{AC}$ | COLLECTOR CURRENT VALUE |
| $I_D, I_{DO}, I_{AC}$ | DRAIN CURRENT VAULE (SAME AS COLLECTOR CURRENT VALUE WHEN CHANNEL IS OPERATED AS A COLLECTOR. SAME AS EMITTER CURRENT WHEN CHANNEL IS OPERATED AS AN EMITTER. |
| $I_E$ | EMITTER CURRENT |
| $V_{GE}$ | GATE VOLTAGE REFERENCED TO EMITTER TERMINAL |
| $V_{DE}$ | DRAIN CONTACT VOLTAGE REFERENCED TO EMITTER TERMINAL. |
| $b_{AC}$ | SAME AS AC BETA (BJT AC CURRENT GAIN) |
| $b_{DC}$ | SAME AS DC BETA (BJT DC CURRENT GAIN) |
| $b_{THG}$ | VALUE OF DC CURRENT GAIN AT $B_G=V_{THG}$ |
| $DV_{TH}$ | D STANDS FOR DELTA AND REFERES TO A CHANGE IN A PARAMETER, IN THIS CASE A CHANGE IN $V_{TH}$ |
| $S_o$ | VALUE OF THE SURFACE RECOMBINATION VELOCITY BELOW THE GATE REGION WHEN $V_G=V_{THG}$ |
| S | SURFACE RECOMBINATION VELOCITY |
| $dg_m/dI_B$ | DERIVATIVE OF $g_m$ with respect to BASE CURRENT |
| $BB_0, BB_1, BB_2, BB_3, BB_4$ | THE DC FOURIER COEFFICIENTS OF DRAIN CURRENT EXPANDED IN A FOURIER SERIES EXPANDED IN TERMS OF THE BASE CURRENT. THE SUBSCRIPTS CORRESPOND TO THE TERM IN THE (BBO IS FIRST COEFFICIENT, C SERIES, ETC.) |
| $BV_0, BV_1, BV_2, BV_3, BV_4$ | DC FOURIER SERIES COEFFICIENTS OF DRAIN CURRENT EXPANDED IN TERMS OF THE GATE VOLTAGE |
| MOSBJT | A SYMBOLIC ACRONYM FOR THE |

| -continued |
|---|
| LIST OF SYMBOLS* |
| DISTRIBUTED CHANNEL BJT DEVICE |

I claim:

1. A merged electronic device consisting of a gate means located above a channel means having a drain contact means located above a base means which is located above an emitter means, said device intended for generating useful electronic characteristics, where said channel means is resistive and can function as a bipolar junction transistor emitter means and collector means, and, when said channel means is functioning as a channel collector means and is resistive, collects a distributed injected current which flows across said base means from said emitter means toward said collector channel means due to a base current applied to said base means, and where said base current may be amplified (or attenuated) by an injection means into said emitter means which injects a current into the base means which is collected by said channel collector means when the channel base junction is reverse biased and which current only is partially collected or not collected by said channel collector means when said channel collector means is partially or wholly forward biased with respect to said base means, where said injected emitter to base current may recombine in part in said base means and or at the surface or interface on the side of the said base means opposite to said emitter means, and where the current density collected by said channel means is distributed along said channel means/base means interface and where said collected current density flowing along said resistive channel means may bias said channel means and where said channel means voltage drop may affect said collection of said injected current density affecting said distributed current collection behavior, thereby affecting the electrical characteristics of the device.

2. An electronic device as described in claim 1 where said channel means functions as an emitter, and where said substrate functions as a collector and where said emitter channel means experiences a distributed behavior due to a current induced voltage drop along said channel means.

3. An electronic device as described in claim 1 where said gate means can be used to modify said channel means resistance.

4. An electronic device as described in claim 2 where said gate means can be used to modify said channel emitter means resistivity.

5. A device as described in claims (1), (2), (3), or (4) where said gate means is an MOS gate.

6. A device such as described in claims (1)–(4) but where said gate means is an MES device.

7. A device as described in claims (1)–(4) where said gate means is a p-n junction gate.

8. A device as described in claims (1)–(4) but where said gate means is absent.

9. A device as described in claims (1)–(8) where said base means is separated by one or more heterojunctions from said emitter means and collector means.

10. A device as described in claims (1)–(9) where said device exhibits a zero transconductance at a value of $V_g(=V_{THG})$ where $V_g$ is the gate to emitter or gate to collector voltage bias.

11. A device as described in claims (1)–(9) where the bias of the channel means by the channel current can create an inhomogeneous BJT behavior with a portion of the device operating in saturation and a portion of the device operating under forward active conditions resulting in non-linear current-current behavior, such as collector current $I_C$ and base current $I_B$, and where said no n-linearities can be used to identify parameter values which are dependent upon an externally applied transduction signal such as from a chemical, force or field.

12. A device such as described by claim 10 where the $V_{THG}$ is dependent upon a shift in the MOS threshold voltage or other threshold voltage which is altered by an externally applied chemical species, force, light, sound or other applied transconduction signal.

13. A device such as described by claims (1)–(10) where said device exhibits a rapidly changing linear or non-linear parameter with change in an applied terminal parameter such as current or voltage with said parameter changes arising from the distributed device behavior and region exhibiting forward active BJT behavior and saturation BJT behavior.

14. A device such as described by claims (1)–(13) where said device displays parameter changes with a change in base DC current $I_{BO}$.

15. A device as described by claims (1)–(14) where said device displays parameter changes which vary with gate voltage $V_g$.

16. A device such as described by claims (14) or (15) where the AC current gain $\beta_{ac}$ is one of the parameters.

17. A device such as described by claims 14 or 15 where said non-linearities are dependent on $I_{BO}$ or $V_g$ where $V_g$ is measured with respect to another device terminal.

18. A device such as described by claim 17 where values of said parameters at particular values of $I_{BO}$ or $V_g$ are sensitive to the particular value of $I_{BO}$ or $V_g$.

19. A device such as described by claims 17 and 18 where said parameters described in claims 17 and 18 are sensitive to a gate threshold voltage.

20. A device as described by claim 19 where said gate threshold voltage is sensitive to the presence of a chemical species or other transduction input signals.

21. A device as described by claim 15 where said parameters are dependent upon magnetic field, force, temperature, light or other externally applied stimulus.

22. A device described by claim 15 where said device has the channel resistivity modulated by an externally applied stimulus.

23. A device described by claim 22 where the channel resistance modulation is caused by light.

24. A device as described by claim 23 where the channel conductivity is modulated by photoconductance modulation.

25. A device as described by claim 23 where the channel conductance is modulated by a photovoltage.

26. A device as described by claims 23, 24 or 25 where the absorbed light has been spatially distributed by wavelength along the said channel means and where said light spatial distribution by wavelength is absorbed by said device and said wavelength dependent light intensities are electrically resolved by said device.

27. A device as described by claim 22 where an applied magnetic field alters the conductance of said channel means.

28. A device as described by claim 11 where a wave propagating along the channel towards or away from the drain is amplified or attenuated dependent upon the relative portions of the device in BJT forward active behavior and in BJT saturation behavior, or a wave propagating at an angle to the channel means is amplified or attenuated and where the degree of amplification or attenuation is affected by external bias.

29. A device as described by claim 28 where the gate means is corrugated.

30. A device as described by claim 28 or claim 29 where the wave is a light wave.

31. A device as described in claims 28, 29 and 30 where the saturated region creates a carrier population inversion layer.

32. A device as described in claims 1-9 where said gate means is chemically sensitive, light sensitive, or pressure or force sensitive, or sensitive to some other transduction means.

33. The device of claim 1 with use of gate shape and size to affect the performance of devices described by claims 1-32.

34. A device of claim 1 described by claims 1-33 where no gate means is used and such that the surface parameters such as surface recombination velocity are altered by chemical or other means.

35. A device described by claim 34 where said channel means surface is exposed to chemical species which alters said exposed surface.

36. A device described by claim 35 where said surface has intentionally introduced defects for binding of chemical species.

37. A device described by claim 36 where said exposed surface is the interface with another material.

38. A device described by claims 35, 36, and or 37 where said chemical species can be removed by photon absorption thereby separation of species from the surface or interface.

39. A device described by claim 38 where different chemical species separation correspond to different photon energies.

40. A device described by claims 1-13 where said gate means absorbs chemical species which change $V_{TH}$ and which can be dissociated from said gate means by photon absorption.

41. A device described by claim 40 where various chemical species are absorbed by said gate means and each species is dissociated from said gate means by a different photon energy.

42. A chemical sensing device such as described in claim 20 where a chemical sensitive gate is separated into N parts and where the N parts each have different chemical sensitivities which can be addressed by appropriate selection of the various terminal's electrical inputs.

* * * * *